(12) United States Patent
Zhao et al.

(10) Patent No.: US 10,398,785 B2
(45) Date of Patent: Sep. 3, 2019

(54) PHARMACEUTICAL COMPOSITIONS CONTAINING TAXANE-CYCLODEXTRIN COMPLEXES, METHOD OF MAKING AND METHODS OF USE

(71) Applicant: MERIDIAN LAB, Buffalo Grove, IL (US)

(72) Inventors: William W. Zhao, Buffalo Grove, IL (US); John K. Thottathil, Buffalo Grove, IL (US); Denise Smith, Buffalo Grove, IL (US); Xiaodong Sun, Buffalo Grove, IL (US); Xiangyu Dong, Buffalo Grove, IL (US)

(73) Assignee: Meridian Lab, Buffalo Grove, IL (US)

( * ) Notice: Subject to any disclaimer, the term of this patent is extended or adjusted under 35 U.S.C. 154(b) by 0 days.

(21) Appl. No.: 15/557,212

(22) PCT Filed: Mar. 14, 2016

(86) PCT No.: PCT/US2016/022247
§ 371 (c)(1),
(2) Date: Sep. 11, 2017

(87) PCT Pub. No.: WO2016/149162
PCT Pub. Date: Sep. 22, 2016

(65) Prior Publication Data
US 2018/0050116 A1 Feb. 22, 2018

Related U.S. Application Data

(60) Provisional application No. 62/304,543, filed on Mar. 7, 2016, provisional application No. 62/133,698, filed on Mar. 16, 2015.

(51) Int. Cl.
| | | |
|---|---|---|
| A61K 9/00 | (2006.01) | |
| A61K 9/08 | (2006.01) | |
| A61K 47/10 | (2017.01) | |
| A61K 47/32 | (2006.01) | |
| C08B 37/16 | (2006.01) | |
| A61K 31/337 | (2006.01) | |
| A61K 47/69 | (2017.01) | |

(52) U.S. Cl.
CPC ........ *A61K 47/6951* (2017.08); *A61K 9/0019* (2013.01); *A61K 9/08* (2013.01); *A61K 31/337* (2013.01); *A61K 47/10* (2013.01); *A61K 47/32* (2013.01); *C08B 37/0015* (2013.01); *A61K 2300/00* (2013.01)

(58) Field of Classification Search
None
See application file for complete search history.

(56) References Cited

U.S. PATENT DOCUMENTS

| | | |
|---|---|---|
| 2006/0105045 A1 | 5/2006 | Buchanan et al. |
| 2010/0048685 A1 | 2/2010 | Ren et al. |

FOREIGN PATENT DOCUMENTS

| | | |
|---|---|---|
| CN | 1676125 A | 10/2005 |
| CN | 101439017 A | 5/2009 |
| KR | 10-2014-0147336 A | 12/2014 |
| KR | 1020140147336 | 12/2014 |
| WO | 2007/136219 | 11/2007 |
| WO | WO 2007136219 A1 | 11/2007 |
| WO | 2008/031285 | 3/2008 |
| WO | 2009/066955 | 5/2009 |
| WO | 2009/066956 | 5/2009 |
| WO | 2012/161520 | 11/2012 |
| WO | WO 2012/161520 | * 11/2012 |
| WO | WO 2014/204172 | * 12/2014 |

OTHER PUBLICATIONS

International Search Report and Written Opinion corresponding to International Patent Application No. PCT/US2016/022247, dated Jun. 28, 2016.

* cited by examiner

*Primary Examiner* — Layla D Berry
(74) *Attorney, Agent, or Firm* — Frank Geo; ABC Patent Service, LLC

(57) ABSTRACT

Pharmaceutical formulations for parenteral administration comprising taxane compounds complexed with cyclodextrins and polyethylene glycol, methods of making the pharmaceutical formulations and methods of treating cancer patients using the pharmaceutical formulations.

19 Claims, 1 Drawing Sheet

Accelerated Aging Stability

| Day | Substance A | Substance B | Substance C | Substance D | Substance E | Substance F | Substance Single Max | Substance Total | pH | Docetaxel (mg/ml) |
|---|---|---|---|---|---|---|---|---|---|---|
| 0 | 0 | 0.06 | 0.53 | 0 | 0 | 0 | 0 | 0.59 | 3.86 | 9.52 |
| 3 | 0 | 0.07 | 0.51 | 0 | 0 | 0 | 0 | 0.58 | 3.86 | 9.52 |
| 7 | 0 | 0.06 | 0.55 | 0 | 0 | 0 | 0.04 | 0.69 | 3.85 | 9.51 |
| 11 | 0 | 0.06 | 0.48 | 0 | 0 | 0 | 0 | 0.54 | 3.86 | 9.52 |
| USP35 Standard | 0.30 | — | 1.3 | 1.5 | 0.5 | 0.5 | 0.2 | 3.5 | | — |

PHARMACEUTICAL COMPOSITIONS CONTAINING TAXANE-CYCLODEXTRIN COMPLEXES, METHOD OF MAKING AND METHODS OF USE

CROSS REFERENCE TO RELATED APPLICATIONS

This application is a national phase filing and claims the priority of International Patent Application No. PCT/US2016/022247, having an International filing date of Mar. 14, 2016, which claims priority to U.S. Provisional Patent Application No. 62/133,698 and 62/304,543, having filing dates of Mar. 16, 2015 and Mar. 7, 2016 respectively. Each of the preceding applications is hereby incorporated by reference in its entirety.

TECHNICAL FIELD

This disclosure relates to pharmaceutical formulations of taxane compounds for parenteral administration, methods of making the pharmaceutical formulations and methods of treating cancer patients using the pharmaceutical formulations.

BACKGROUND

Taxanes are diterpenes that are widely used in chemotherapy. They were originally discovered in plants of the genus *Taxus* (yews) and were first derived from these natural sources. Several are now chemically synthesized. Among the taxanes, the best known are paclitaxel (TAXOL) and docetaxel (TAXOTERE), which is a semisynthetic analog of paclitaxel. Taxanes exert their anti-cancer activity by inhibiting tubulin depolymerization in cells, thus inhibiting mitosis.

Parenteral administration by injection is the typical route of administration of taxanes. However, taxanes are substantially insoluble in water and in other commonly used medicinal parenteral organic solvents, which has presented a challenge to formulation for pharmaceutical use. Docetaxel is typically formulated with POLYSORBATE 80 (Tween 80, a nonionic surfactant and emulsifier) to improve solubility. Paclitaxel is typically formulated with the nonionic surfactant CREMOPHOR EL (polyoxyethylated castor oil). Increased toxicity, including hypersensitivity reactions, anaphylaxis and other serious side effects are associated with these excipients. Pre-medication and additional treatment to prevent hypersensitivity is therefore often necessary. Such additional treatment includes hormone treatment, steroid medications, dexamethasone, diphenhydramine and cimetidine. In addition, the patient must be monitored closely for severe allergic reactions, such as observation of blood pressure, breathing rate, and heart rate. Increased toxicity and side effects sometimes restrict the continuation and completion of taxane treatments thus limiting its effectiveness.

The currently available pharmaceutical formulations of taxanes also suffer from unsatisfactory stability. For example, the docetaxel formulation has low stability, and must be stored at or below room temperature protected from light. Alternatively, they need to be stored as a lyophilized solid prior to re-constitution to a liquid for patient administration. In the IV solution docetaxel has a tendency to precipitate, and requires careful handling procedures such as to avoid shaking.

Efforts to improve the safety and efficacy of taxane pharmaceutical formulations, particularly with paclitaxel and docetaxel, have generally focused on liposomal formulations, nano-granules, cross-linking with albumin, and formulation with cyclodextrin based complexes. It has been shown that complexes with cyclodextrin enhance docetaxel stability, enhance its solubility, and can also enhance drug activity and reduce toxic side effects. However, the solubility of docetaxel after complexing with cyclodextrin is still relatively low, and is inconvenient for clinical use due to a requirement for a substantial amount of solvent to solubilize the complex. Further, because cyclodextrin can degrade ester compounds such as docetaxel, stability can be compromised.

Formulations of docetaxel and paclitaxel requiring reduced amounts organic solvent and cyclodextrin have been reported. See U.S. Pat. Nos. 8,481,511 and 8,426,385. These formulations of either docetaxel or paclitaxel in complexes with hydroxypropyl-β-cyclodextrin (HP-β-CD) and/or sulfobutylether-β-cyclodextrin (SBE-β-CD) provide improved water-solubility and stability, as demonstrated by the Ka. To prepare the compositions, paclitaxel or docetaxel is dissolved in ethanol and added to an aqueous solution of cyclodextrin derivatives, stirring until the taxane is dissolved. Ethanol is then removed via reduced pressure to obtain the complex in liquid form. However, the liquid form is physico-chemically unstable and must be lyophilized to obtain a stable solid (i.e., a lyophilized powder) composition. Chemical and physical stability in liquid form, after reconstitution, is limited to 2-3 hours. Because the powder must be reconstituted before use, the risk of exposure of medical personnel to these cytotoxic compounds is increased. In addition, the present inventors have observed that the lyophilized powder cannot be reconstituted in normal saline, as the API has limited physical stability in saline and quickly precipitates. It can however, be reconstituted in dextrose.

Although there has been some success in improving biocompatibility, in vivo tolerance, solubilization and formulation stability, there is still a need for further improvements in these parameters for pharmaceutical taxane compositions, particularly in parenteral formulations. The present invention addresses these needs. In contrast to the prior art cyclodextrin/taxane powders, the stable liquid pharmaceutical compositions comprising taxane/β-cyclodextrin complexes disclosed herein, based on accelerated aging studies, are expected to remain chemically and physically stable at temperatures from 0° C. to ambient temperature for at least one year, and may be diluted for use in either normal saline or dextrose. The present liquid pharmaceutical compositions also represent significant improvements over the prior art in that they do not contain toxic solubilizers such as CREMOPHOR EL and POLYSORBATE 80 (aka TWEEN 80).

SUMMARY

In a first aspect the invention is directed to liquid pharmaceutical compositions comprising complexes of a taxane with a β-cyclodextrin or a β-cyclodextrin derivative (a "taxane/β-cyclodextrin complex"), polyethylene glycol (PEG), an alcohol suitable for parenteral administration, and water. In certain embodiments, the liquid pharmaceutical compositions may comprise a selected amount by weight of the taxane, 5 to 100 parts by weight (p.b.w.) of the β-cyclodextrin or β-cyclodextrin derivative relative to the taxane, 10 to 50 p.b.w. of the PEG relative to the taxane, and 5 to 60 p.b.w. of the alcohol relative to the taxane. The remainder of the composition is water, such as pyrogen-free water suitable for injection. Stated on the basis of the weight ratios of the components of the liquid pharmaceutical compositions, the ratio of taxane to β-cyclodextrin or β-cyclodextrin derivative to PEG may be in the range of 1:5:50 to 1:100:10, with alcohol suitable for parenteral administration present in a weight ratio of 5 to 60 relative to taxane and water in a weight ratio of 10 to 50 relative to taxane. In further specific embodiments of the foregoing liquid pharmaceutical compositions, the β-cyclodextrin may be present at 40-100 p.b.w., the polyethylene glycol may be present at 10-30 p.b.w., the alcohol may be present at 5-40 p.b.w., and/or water may be present at 10-50 p.b.w. relative to the weight of taxane. Specific examples include liquid pharmaceutical compositions comprising a weight ratio of taxane to β-cyclodextrin or β-cyclodextrin derivative to PEG of 1:50: 30, 1:40:30, or 1:60:20. Further specific examples include liquid pharmaceutical compositions comprising a weight ratio of taxane to β-cyclodextrin or β-cyclodextrin derivative to PEG to alcohol to water of 1:50:30:20:10, 1:40:30: 30:20, or 1:60:20:5:30.

In a further embodiment, the liquid pharmaceutical compositions may further comprise one or more of a weak organic acid, an antioxidant, and a chelator. In a specific embodiment, the alcohol suitable for parenteral administration may be selected from the group consisting of ethanol, benzyl alcohol, and combinations thereof; the weak organic acid may be citric acid, acetic acid, or phosphoric acid; the antioxidant may be selected from the group consisting of sodium bisulfite, sodium metabisulfite and combinations thereof, and; the chelator may be disodium edetate. In a further specific embodiment, the liquid pharmaceutical composition may comprise 2-5 p.b.w. of the weak organic acid (to adjust the final pH as desired), 0.01-0.1 p.b.w. of the antioxidant, and 0.01-0.5 p.b.w. of the chelator.

In any of the foregoing embodiments of the liquid pharmaceutical compositions, the taxane may be paclitaxel, docetaxel, cabazitaxel, ortataxel, tesetaxel or a combination thereof. In any of the foregoing embodiments of the liquid pharmaceutical formulation, the β-cyclodextrin may be selected from the group consisting of sulfobutylether-β-cyclodextrin, hydroxypropyl-β-cyclodextrin, hydroxypropyl-sulfobutylether-β-cyclodextrin, acet-β-cyclodextrin, methyl-β-cyclodextrin, 2,6-dimethyl-β-cyclodextrin, β-cyclodextrin and combinations thereof. In any of the foregoing embodiments, the alcohol suitable for parenteral administration may be selected from the group consisting of ethanol, benzyl alcohol, and combinations thereof. In any of the foregoing embodiments, the polyethylene glycol may be a low molecular weight PEG, and in specific embodiments may be selected from the group consisting of PEG 200, PEG 300, PEG 400, PEG 600, and combinations thereof.

Another embodiment of any of the foregoing liquid pharmaceutical compositions provides a liquid pharmaceutical compositions comprising complexes of a taxane with a β-cyclodextrin or a β-cyclodextrin derivative (a "taxane/β-cyclodextrin complex"), polyethylene glycol (PEG), an alcohol suitable for parenteral administration, a polyvinylpyrrolidone (aka povidone or PVP) and water. In some embodiments the povidone has an average molecular weight of 2000-3000 g/mol. In some embodiments the liquid pharmaceutical compositions comprise a weight ratio of taxane to povidone of 1:1 to 1:10. In a specific embodiment the weight ratio of taxane to povidone is 1:5. Specific examples include liquid pharmaceutical compositions comprising a weight ratio of taxane to β-cyclodextrin or β-cyclodextrin derivative to PEG to povidone of 1:50:30:5, 1:40:30:5, or 1:60:20:5. Further specific examples include liquid pharmaceutical compositions comprising a weight ratio of taxane to β-cyclodextrin or β-cyclodextrin derivative to PEG to povidone of 1:50:20:5 and 1:60:15:5. Still other specific examples include liquid pharmaceutical compositions comprising a weight ratio of taxane to β-cyclodextrin or β-cyclodextrin derivative to PEG to povidone of 1:40:20:5 and 1:30:30:5.

In a second aspect, the invention provides methods of making the liquid pharmaceutical compositions described above. The methods may comprise the steps of:
a) dissolving a taxane in an alcohol suitable for parenteral administration to form a taxane solution;
b) dispersing a low molecular weight polyethylene glycol in water to form a dispersion, and dissolving the β-cyclodextrin or β-cyclodextrin derivative in the dispersion;
c) optionally, dispersing povidone into the dispersion obtained in step (b);
d) combining the taxane solution obtained in step (a) and the dispersion obtained in step (b) or (c);
e) adjusting the combination obtained in step (d) to a final volume with the alcohol or water; and
f) optionally, adjusting pH of the final volume by addition of a weak organic acid.

In a specific embodiment, the method of making the liquid pharmaceutical compositions described above comprises:
a) combining the taxane with a portion of the alcohol suitable for parenteral administration and mixing until the taxane is dissolved;
b) dispersing the polyethylene glycol in the water;
c) adding the β-cyclodextrin, the β-cyclodextrin derivative, or mixture thereof, to the polyethylene glycol/water dispersion obtained in step (b), and mixing until the β-cyclodextrin or the β-cyclodextrin derivative is dissolved;
d) optionally, dispersing povidone into the mixture obtained in step (c);
e) adding a remaining portion of the ethanol to the mixture obtained in step (c) or (d) and mixing to form a homogenous solution; and
f) adding the taxane/alcohol mixture obtained in step (a) to the solution obtained in step (e) while mixing under an inert atmosphere to obtain a homogeneous solution of the liquid pharmaceutical composition.

Certain embodiments of the methods of making the pharmaceutical compositions may include a further step of sterilizing the homogeneous solution obtained. The sterilization may be filter sterilization. In further embodiments, in step (a), the taxane may be combined with ¼ to ½ of the total amount of alcohol suitable for parenteral administration in the final formulation. In other embodiments, the method may further comprise the step of mixing one or more of a weak organic acid, an antioxidant and a chelator in the water in step (b). In some embodiments, the steps (c), (d), (e) and (f) of the process may be carried out under an inert atmosphere such as nitrogen. In a modification of such embodiments, all steps of the process are carried out under an inert atmosphere such as nitrogen. In certain embodiments, the compounds and their amounts used in the methods of making the liquid pharmaceutical compositions may be those discussed above with respect to the liquid pharmaceutical composition, per se.

In a third aspect, the invention provides methods of treating cancer in a patient by parenteral administration to the cancer patient of any of the foregoing embodiments of the liquid pharmaceutical compositions, in an amount sufficient to treat the cancer. Accordingly, the invention also provides use of the liquid pharmaceutical formulation of any of the foregoing embodiments of the liquid pharmaceutical compositions for the treatment of cancer

BRIEF DESCRIPTION OF THE DRAWINGS

The FIGURE shows the results of accelerated aging stability studies for an exemplary liquid pharmaceutical composition as described herein.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein the term "taxane" refers, individually and collectively, to diterpene compounds of the taxane family. Included are naturally occurring taxanes, derivatives of such naturally occurring taxanes, semi-synthetic taxanes and synthetic taxanes.

As used herein the term "taxane/β-cyclodextrin complex" refers to the complex formed by the interaction of a β-cyclodextrin or a derivative of a β-cyclodextrin molecule having a 7-membered sugar ring (β-cyclodextrin ring) with a hydrophobic diterpene which is a member of the taxane drug family (including naturally occurring compounds and their derivatives, semi-synthetic compounds, and synthetic compounds) in a manner which improves the solubility of the taxane in aqueous media.

As used herein, the term "physical stability" refers to an absence of: precipitate formation, turbidity, opaqueness, or coagulation/gelatinous formation in the liquid pharmaceutical taxane/β-cyclodextrin complex compositions over time.

As used herein, the term "chemical stability" refers to an absence of chemical impurity formation and/or an absence of taxane degradation in the liquid pharmaceutical taxane/β-cyclodextrin complex compositions over time.

As used herein the term "parenteral administration" refers to administration of a composition to a patient via injection or infusion. Included are intravenous injection, subcutaneous injection and intramuscular injection. Also included is infusion, which is typically administration via the intravenous route over a period of time. "Suitable for parenteral administration" refers to acceptable safety of a component when parenterally administered, which is typically established by regulatory approval of the component for such use.

As used herein the term "treatment" of cancer and its equivalents refers to reducing the symptoms or extent of cancer in a patient by administration of a drug or drug formulation. Treatment may also include curing the cancer or reducing the cancer burden to levels below detection limits, or preventing its recurrence.

In certain embodiments, the liquid pharmaceutical compositions described herein comprise taxane complexes with a β-cyclodextrin or β-cyclodextrin derivative, polyethylene glycol (PEG), an alcohol suitable for parenteral administration, and water. The taxane portion of the taxane/β-cyclodextrin complex may be any naturally-occurring, semi-synthetic or synthetic hydrophobic taxane known in the art, including those that have regulatory approval for clinical use (e.g., paclitaxel, docetaxel, and cabazitaxel) as well as those that are in development or otherwise known in the art. Examples of suitable taxanes that are of scientific interest but are not currently approved for commercial use include DJ-927 (tesetaxel), ortataxel, XRP9881, DHA-paclitaxel, and BMS-184476). In specific embodiments, the liquid pharmaceutical compositions described herein comprise paclitaxel, docetaxel, or a combination thereof, in the taxane/β-cyclodextrin-derivative complex.

The β-cyclodextrin portion of the taxane/β-cyclodextrin complex may be any suitable β-cyclodextrin or derivative of β-cyclodextrin. Specific examples include sulfobutylether-β-cyclodextrin (SBE-β-CD) (which may or may not be as its sodium salt), hydroxypropyl-β-cyclodextrin (HP-β-CD), hydroxypropyl-sulfobutylether-β-cyclodextrin (HP-SBE-β-CD), acet-β-cyclodextrin, methyl-β-cyclodextrin, 2,6-dimethyl-β-cyclodextrin, β-cyclodextrin and combinations thereof. In specific embodiments, the liquid pharmaceutical compositions described herein comprise sulfobutylether-β-cyclodextrin sodium, hydroxypropyl-β-cyclodextrin, hydroxypropyl-sulfobutylether-β-cyclodextrin or a combination thereof, in the taxane/β-cyclodextrin complex.

The polyethylene glycol component of the liquid pharmaceutical compositions described herein may be any pharmaceutically acceptable PEGs known in the art that are suitable for pharmaceutical applications and that are suitable to provide improved physical and chemical stability to the composition. In certain embodiments, the PEG component of the compositions is a low molecular weight PEG which has a molecular weight of 2000 daltons or less. In a particular embodiment, the PEG component of the composition has a molecular weight of from about 200 daltons to about 800 daltons. In a specific embodiment, the PEG component of the composition has a molecular weight of 300 daltons, 400 daltons, or 600 daltons.

The alcohol suitable for parenteral administration used in the liquid pharmaceutical compositions described herein may be any alcohol that is suitably safe for parenteral administration (whether diluted with water or undiluted). Typically, the alcohol will be approved by regulatory authorities for parenteral use. Examples of suitable pharmaceutically acceptable alcohols include ethanol, benzyl alcohol, and combinations thereof. In a specific embodiment, the alcohol component of the liquid pharmaceutical compositions described herein is ethanol.

The taxane/β-cyclodextrin complex, low molecular weight PEG, and alcohol suitable for parenteral administration are the basic components of the liquid pharmaceutical compositions. Typically, the remainder of the composition is water, for example water for injection.

In certain embodiments, the pH of the liquid pharmaceutical composition may optionally be adjusted by inclusion of a weak organic acid in an amount sufficient to further improve the stability of the taxane. Taxanes typically show improved stability in the acidic pH range. If necessary or desired, the pH may be adjusted into the range of 3-8, or 4-7, or 3.5-4 by addition of the weak organic acid. The weak organic acid added to adjust the pH may be, for example, citric acid, acetic acid, ascorbic acid, aspartic acid, formic acid, lactic acid, glutamic acid, phosphoric acid or succinic acid. However, suitable compositions in the range of pH 3.5-4 can often be obtained without adjustment of the pH with weak organic acid. The liquid pharmaceutical compositions described herein may also optionally contain one or more antioxidants, as is known in the art. Any natural or synthetic antioxidant that is suitable for parenteral administration may be included in the compositions. Examples of suitable antioxidants include sodium bisulfite, sodium metabisulfite, and combinations thereof. The liquid pharmaceutical compositions described herein may also optionally contain one or more chelator compounds as is known in the art that are suitable for parenteral administration. Examples of suitable chelators include ethylenediaminetetraacetic acid salts (EDTA, aka: disodium edetate; calcium edetate). In a specific example, the chelator used in the liquid pharmaceutical compositions described herein is disodium EDTA. As discussed above, the remainder of the composition after selection of the base component amounts and the amounts of optional components (if any) is water, for example water for injection.

A specific embodiment of the liquid pharmaceutical compositions described above is a composition which comprises the base components (i.e., taxane/β-cyclodextrin complex, low molecular weight polyethylene glycol, alcohol suitable for parenteral administration, and water) as follows: a selected amount of the taxane by weight, 5 to 200 p.b.w. of the β-cyclodextrin or β-cyclodextrin derivative with respect to the taxane, 50 to 20 p.b.w. of the polyethylene glycol relative to the taxane, 5 to 60 p.b.w. of the alcohol suitable for parenteral administration relative to the taxane, and 10 to 50 p.b.w. of the water relative to the taxane. Any or all of the optional components of the compositions may be added to this base formulation in the amounts disclosed herein. A further specific embodiment of the liquid pharmaceutical compositions comprise a selected amount of the taxane by weight, 5 to 100 p.b.w. of the β-cyclodextrin or β-cyclodextrin derivative with respect to the taxane, 50 to 10 p.b.w. of the polyethylene glycol relative to the taxane, 5 to 60 p.b.w. of the alcohol suitable for parenteral administration relative to the taxane, and 10 to 50 p.b.w. of the water relative to the taxane. As a specific example, the liquid pharmaceutical compositions may comprise 1 p.b.w. taxane, 40 to 60 p.b.w. of the β-cyclodextrin or β-cyclodextrin derivative relative to the taxane, 20 to 30 p.b.w. of the polyethylene glycol relative to the taxane, 5 to 30 p.b.w. of the alcohol suitable for parenteral administration relative to the taxane, and 10 to 30 p.b.w. water relative to the taxane.

Weight ratios of the components of certain specific embodiments of the liquid pharmaceutical compositions include 1:40:30, 1:50:30 or 1:60:20 (taxane:β-cyclodextrin or β-cyclodextrin derivative:PEG). Such embodiments include; for example, weight ratios of 1:40:30:30:20 (taxane:β-cyclodextrin or β-cyclodextrin derivative:PEG:alcohol:water), 1:50:30:20:10 (taxane:β-cyclodextrin or β-cyclodextrin derivative:PEG:alcohol:water), and 1:60:20:5:30 (taxane:β-cyclodextrin or β-cyclodextrin derivative:PEG:alcohol:water).

A further specific embodiment of any of the foregoing liquid pharmaceutical compositions is a composition which further comprises optional components as follows: 2-5 p.b.w. of a weak organic acid relative to the taxane (to adjust the final pH), 0.01-0.1 p.b.w. of an antioxidant relative to the taxane, and/or 0.01-0.5 p.b.w. of a chelator relative to the taxane.

In a further embodiment, any of the foregoing liquid pharmaceutical compositions may optionally further comprise a soluble polyvinylpyrrolidone (aka povidone or PVP, for example povidone PF12 or PF17). The inclusion of povidone in the composition further improves its chemical and physical stability. The selected soluble povidone is preferably suitable for parenteral use, i.e., with low endotoxin levels. Examples include Kollidon® soluble povidones from BASF, such as Kollidon® PF12 ($M_w$ 2,000-3,000), Kollidon® PF17 ($M_w$ 7,000-11,000), and mixtures thereof. Other suitable low-endotoxin soluble povidones are also available commercially, including Plasdone™ C-12 (nominal $M_w$ 4,000) and Plasdone™ C-17 (nominal $M_w$ 10,000) from Ashland. Because it is difficult to determine the molecular weight of povidone polymers directly, the K-value has been adopted to classify the various molecular weights of povidones. The K-value is a function of the average degree of polymerization and the intrinsic viscosity of the polymer, and is calculated from the kinematic viscosity of an aqueous polymer solution. Examples of povidones for use in the invention, characterized by their K-value, include povidones having K-values of 10.2-13.8, povidones having K-values of 15.5-17.5, and mixtures thereof. Specific examples include povidones having K-values of about 12, povidones having K-values of about 17, and mixtures thereof.

In some embodiments the liquid pharmaceutical compositions comprise a weight ratio of taxane to povidone of 1:1 to 1:10. In a specific embodiment the weight ratio of taxane to povidone is 1:5. Specific examples include liquid pharmaceutical compositions comprising a weight ratio of taxane to β-cyclodextrin or β-cyclodextrin derivative to PEG to povidone of 1:50:30:5, 1:40:30:5, or 1:60:20:5. Further specific examples include liquid pharmaceutical compositions comprising a weight ratio of taxane to β-cyclodextrin or β-cyclodextrin derivative to PEG to povidone of 1:50:20:5 and 1:60:15:5. Other specific examples include liquid pharmaceutical compositions comprising a weight ratio of taxane to β-cyclodextrin or β-cyclodextrin derivative to PEG to povidone of 1:40:20:5 and 1:30:30:5.

The liquid pharmaceutical compositions described herein are physically and chemically stable as liquid solutions for an extended period of time. That is, under conditions of accelerated aging the impurities remain low (i.e., below allowable limits set by the United States Pharmacopeia USP35 standards for taxanes) and the taxane shows no decomposition, precipitation or turbidity formation. The compositions therefore provide the advantage of long-term stable storage in a liquid form that reduces risk to medical personnel handling the compositions. To use the liquid pharmaceutical taxane/β-cyclodextrin compositions for treatment of a cancer patient, the concentrated composition as described above is diluted to the appropriate dose in a pharmaceutically acceptable aqueous medium (for example, in an IV or infusion bag at the patient bed-side) and delivered parenterally to the patient for treatment of the cancer. The reconstitution and mixing step that increases exposure of medical personnel when using lyophilized powder formulations is therefore eliminated. Also eliminated are problems associated with incomplete dissolution, precipitation after dissolution and frothing during dissolution, with the avoidance of very sensitive shaking/mixing restrictions required for prior art taxane compositions). Persons skilled in the art can determine the effective dose and administration protocol to achieve treatment of specific cancers using the liquid pharmaceutical compositions described herein. Accordingly, use of the liquid pharmaceutical compositions described herein for treatment of cancer is an embodiment of the invention. Generally, the route of delivery of the diluted composition will be by intravenous injection or intravenous infusion.

The present liquid pharmaceutical compositions also have the advantage that they can be diluted in either saline or dextrose. This is in contrast to the lyophilized powders disclosed in U.S. Pat. Nos. 8,481,511 and 8,426,385, which form stable solutions only when reconstituted in dextrose, i.e., reconstitution in saline results in precipitation of the taxane. Because the liquid pharmaceutical compositions described herein can be diluted directly into an infusion bag and do not contain toxic solubilizers and emulsifiers, treatment of patients using the liquid pharmaceutical compositions substantially reduces the risk of toxicity to both medical personnel (who must handle the compositions) and to patients (who are at risk for potentially life-threatening hypersensitivity reactions to solubilizers used in the prior art).

In one aspect, the liquid pharmaceutical compositions disclosed herein may be used in methods for treating cancer patients by administering any of the foregoing liquid pharmaceutical formulations to a cancer patient in an amount sufficient for cancer treatment. Accordingly, it is also to be understood that embodiment of such methods or treatment include use of any of the foregoing liquid pharmaceutical formulations for treatment of cancer. In general, the amount of taxane administered and the duration of treatment are within the skill and knowledge of the medical practitioner. However, it is to be understood that the present taxane formulations do not need to be reconstituted prior to administration. That is, the present liquid pharmaceutical taxane formulations can simply be diluted using saline or dextrose to obtain the desired taxane concentration for administration to the patient, including dilution by direct injection of the concentrate into the patient's IV bag.

The liquid pharmaceutical compositions described herein may be prepared by the following general method:
a) dissolving a taxane in an alcohol suitable for parenteral administration to form a taxane solution;
b) dispersing a low molecular weight polyethylene glycol in water to form a dispersion, and dissolving a β-cyclodextrin or β-cyclodextrin derivative in the dispersion;
c) optionally, dispersing povidone into the dispersion obtained in step (b);
d) combining the taxane solution obtained in step (a) and the dispersion obtained in step (b) or (c) to form a homogeneous solution; and
e) if needed, adjusting the homogeneous solution obtained in step (d) to a final volume with the alcohol or water.

The liquid pharmaceutical compositions described herein may also be prepared by the following specific method:
a) combining the taxane with a portion of the alcohol and mixing until the taxane is dissolved;
b) dispersing the polyethylene glycol in the water;
c) adding the β-cyclodextrin, or mixture thereof, to the polyethylene glycol/water dispersion obtained in step (b), and mixing until the β-cyclodextrin is dissolved;
d) optionally, dispersing povidone into the mixture obtained in step (c);
e) adding a remaining portion of the alcohol to the mixture obtained in step (c) or (d) and mixing to form a solution; and
f) adding the taxane/alcohol mixture obtained in step (a) to the solution obtained in step (e) while mixing to obtain a homogeneous solution of the liquid pharmaceutical composition.

In certain embodiments, steps (c), (d), (e) and (f) of the above method may be conducted under an inert atmosphere, for example nitrogen or argon. In alternative embodiments all of the steps of the preparations methods may be conducted under an inert atmosphere, for example nitrogen or argon.

The portion of the alcohol suitable for parenteral administration that is added in step (a) in some embodiments may be ¼ to ½ of the total amount in the final composition. The remaining amount of alcohol may then be added in step (e). The ratio of each component used in the method is calculated based on the desired composition of the final product, as discussed above and the amount of each component used in the method is calculated based on the desired final amount of the final product, as discussed above. Any or all of the steps of the process may be carried out under an inert atmosphere such as nitrogen or argon. In contrast to the prior art lyophilized powder formulations discussed above, the alcohol suitable for parenteral administration is not removed in the manufacturing process and is a component of the final liquid pharmaceutical compositions described herein.

If any or all of the optional components of the composition (weak organic acid, antioxidant and/or chelator) are to be included in the liquid pharmaceutical composition, they may be added to the water in step (b) prior to addition of the polyethylene glycol, and mixed to dissolve. The PEG may then be dispersed in the solution of water and optional component(s). The weak organic acid may also be added at to the homogeneous solution at the end of the process to adjust the final pH to the desired value.

In certain embodiments, the water used for preparation of the liquid pharmaceutical compositions may be water for injection (WFI), which is pyrogen-free. It may still be desirable, however, to sterilize the final product before dispensing it into individual vials and sealing. Sterilization may be accomplished by filter sterilization, for example by filtration through a 0.22 µm membrane filter.

EXAMPLES

Accelerated Aging Stability Studies

A liquid pharmaceutical composition as described above, comprising ~10 mg/mL docetaxel was diluted and subjected to accelerated aging at 40° C. for eleven days. The levels of impurities as specified by USP35 (United States Pharmacopeia 35) for taxane compositions were analyzed by HPLC at regular intervals. Stability was tested at 6 hours on day 0. Impurity levels in the liquid pharmaceutical compositions were compared to the allowable level according to the USP35 standard. The results are shown in FIG. 1. It can be seen that all impurities (Substances A-F) are substantially below the USP35 limits for the entire 1-day period of accelerated aging. In addition, the impurities that are present do not increase over the 11 days of testing, and no new impurities or degradation products were formed, indicating that the composition is chemically stable. The composition was also physically stable, as no precipitate or turbidity was formed.

In addition, the concentration of docetaxel remained constant at 9.52 mg/mL throughout the 11 days of accelerated aging. This confirms that the taxane does not decompose even at 40° C. for 11 days.

Stability of Exemplary Formulations

Various liquid pharmaceutical compositions were prepared as described above, comprising weight ratios of docetaxel to cyclodextrin to PEG from 1:5:50 to 1:100:10. pH of the formulations was about 3.5-4.0 without adjustment. Stability at 40° C. with respect to the level of impurities was analyzed by HPLC at regular intervals as specified by USP35 (United States Pharmacopeia 35) for taxane compositions. Impurity levels in the liquid pharmaceutical compositions were compared to the allowable level according to the USP35 standard. The time point at which the levels of impurities exceeded the allowable level for each of the compositions is shown in Table 1:

TABLE 1

Weight Ratios of Drug to Excipients

| Example | Docetaxel | cyclo-dextrin | PEG300 | ethanol | water | 40° C. Stability (Undiluted) | Diluted Stability (Ambient) |
|---|---|---|---|---|---|---|---|
| 1 | 1 | 100 | 10 | 10 | 50 | 6 mo | >=6 h |
| 2 | 1 | 80 | 20 | 40 | 40 | 6 mo | >=6 h |
| 3 | 1 | 60 | 20 | 5 | 30 | 6 mo | >=6 h |
| 4 | 1 | 50 | 30 | 20 | 10 | 6 mo | 6 h |
| 5 | 1 | 40 | 30 | 30 | 20 | 6 mo | 5 h |
| 6 | 1 | 30 | 40 | 40 | 15 | 5 mo | 4 h |
| 7 | 1 | 20 | 50 | 40 | 15 | 5 mo | 2 h |
| 8 | 1 | 10 | 50 | 50 | 15 | 4 mo | 1 h |
| 9 | 1 | 5 | 50 | 60 | 10 | 2 mo | 0.5 h |

Physical stability of the samples was confirmed visually and no turbidity, cloudiness or precipitation was observed during the time periods in which the samples were chemically stable. Formulations comprising at least 1:5:50 parts by weight of docetaxel:cyclodextrin:PEG300 exhibited extended chemical stability on accelerated aging (2 months). Chemical stability could be increased to at least six months by increasing the proportion of cyclodextrin and reducing the proportion of PEG300 (formulations having weight ratios from 1:40:30 to 1:100:10). Intermediate duration of chemical stability was obtained with ratios from 1:10:50 to 1:30:40. Table 2 shows the formulations tested in Table 1 normalized to a single vial containing 20 mg. of docetaxel:

TABLE 2

Normalized to single vial (20 mg)

| Example | Docetaxel | cyclo-dextrin | PEG 300 | ethanol | water | 40° C. Stability | Diluted stability |
|---|---|---|---|---|---|---|---|
| 1 | 20 mg | 2 g | 0.2 g | 0.2 g | 1 g | 6 mo. | >=6 h |
| 2 | 20 mg | 1.6 g | 0.4 g | 0.8 g | 0.8 g | 6 mo. | >=6 h |
| 3 | 20 mg | 1.2 g | 0.4 g | 0.1 g | 0.6 g | 6 mo. | >=6 h |
| 4 | 20 mg | 1 g | 0.6 g | 0.4 g | 0.2 g | 6 mo. | 6 h |
| 5 | 20 mg | 0.8 g | 0.6 g | 0.6 g | 0.4 g | 6 mo. | 5 h |
| 6 | 20 mg | 0.6 g | 0.8 g | 0.8 g | 0.3 g | 5 mo. | 4 h |
| 7 | 20 mg | 0.4 g | 1 g | 0.8 g | 0.3 g | 5 mo. | 2 h |
| 8 | 20 mg | 0.2 g | 1 g | 1 g | 0.3 g | 4 mo. | 1 h |
| 9 | 20 mg | 0.1 g | 1 g | 1.2 g | 1 g | 2 mo. | 0.5 h |

Pharmaceutical Compositions Containing Povidone

Pharmaceutical compositions were prepared as above with the addition of povidone PF12. Compositions comprised docetaxel:ethanol:PEG300:cyclodextrin:povidone in weight ratios as shown in Table 3.

TABLE 3

| Example | Docetaxel | Povidone PF12 | cyclo-dextrin | PEG 300 | ethanol | Stability |
|---|---|---|---|---|---|---|
| M | 1 | 5 | 45 | 0 | 18 | API solidified during stirring. |
| N | 1 | 5 | 60 | 15 | 30 | Completely dissolved after 30 min. Reconstitution stability ≥6 hr. |
| O | 1 | 5 | 50 | 20 | 24 | Completely dissolved after 30 min. Reconstitution stability ≥3.5 hr. Impurity level acceptable at 25° C. after 6 months. |

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A liquid pharmaceutical composition comprising:
    a taxane complexe with a β-cyclodextrin derivative, wherein the β-cyclodextrin derivative is selected from the group consisting of sulfobutylether-β-cyclodextrin sodium, hydroxypropyl-sulfobutylether-β-cyclodextrin, and combinations thereof;
    a low molecular weight polyethylene glycol (PEG);
    an alcohol suitable for parenteral administration; and
    water.

2. The liquid pharmaceutical composition of claim 1 which comprises a selected amount of the taxane by weight, about 5 to about 100 parts by weight (p.b.w.) of the β-cyclodextrin derivative relative to the taxane, about 10 to about 50 p.b.w. of the PEG relative to the taxane, about 5 to about 60 p.b.w. of the alcohol relative to the taxane, and about 10 to about 50 p.b.w. of the water relative to the taxane.

3. The liquid pharmaceutical composition of claim 2 which comprises a weight ratio of taxane to β-cyclodextrin derivative to PEG of about 1:50:30, about 1:40:30, about 1:60:20, about 1:80:20, or about 1:100:10.

4. The liquid pharmaceutical composition of claim 3 which comprises a weight ratio of taxane β-cyclodextrin derivative to PEG to alcohol to water of about 1:50:30:20:10, about 1:40:30:30:20, about 1:60:20:5:30, about 1:80:20:40:40, or about 1:100:10:10:50.

5. The liquid pharmaceutical composition of claim 4 further comprising a soluble povidone suitable for parenteral use.

6. The liquid pharmaceutical composition of claim 5, wherein the povidone is selected from the group consisting of povidones having a K-value of about 10.2-13.8, povidones having a K-value of about 15.5-17.5, and mixtures thereof.

7. The liquid pharmaceutical composition of claim 6, wherein the povidone has a K-value of about 12 or a K-value of about 17.

8. The liquid pharmaceutical composition of claim 7, wherein the weight ratio of taxane to povidone is about 1:5.

9. The liquid pharmaceutical composition of claim 8, further comprising one or more of a weak organic acid, an antioxidant, and a chelator.

10. The liquid pharmaceutical composition of claim 9, wherein the antioxidant is selected from the group consisting of sodium bisulfite, sodium metabisulfite, and combinations thereof.

11. The liquid pharmaceutical composition of claim 9, wherein the weak organic acid is citric acid.

12. The liquid pharmaceutical composition of claim 10, which comprises about 2-5 p.b.w. of the weak organic acid relative to the taxane, about 0.01-0.1 p.b.w. of the antioxidant relative to the taxane, and/or about 0.01-0.5 p.b.w. of the chelator relative to the taxane.

13. The liquid pharmaceutical composition of claim 11, wherein the taxane is selected from the group consisting of paclitaxel, docetaxel, and combinations thereof.

14. The liquid pharmaceutical composition of claim 13, wherein the polyethylene glycol is selected from the group consisting of PEG200, PEG300, PEG400, PEG600, and combinations thereof.

15. The liquid pharmaceutical composition of claim 13, wherein the alcohol suitable for parenteral administration is selected from the group consisting of ethanol, n-propanol, isopropanol, benzyl alcohol, and combinations thereof.

16. The liquid pharmaceutical composition of claim 1, which comprises about 40 to about 100 p.b.w. of β-cyclodextrin derivative relative to the taxane and about 10 to about 30 p.b.w. of the PEG relative to the taxane.

17. A method of making a liquid pharmaceutical composition, comprising:
   (a) dissolving a taxane in an alcohol suitable for parenteral administration to form a taxane solution;
   (b) dispersing a low molecular weight polyethylene glycol in water to form a dispersion, and
   (c) dissolving a β-cyclodextrin or β-cyclodextrin derivative in the dispersion; optionally, dispersing povidone into the dispersion obtained in step (b);
   (d) combining the taxane solution obtained in step (a) and the dispersion obtained in step (b) or (c) to obtain a homogeneous solution; and optionally, adjusting the homogeneous solution obtained in step (d) to a final volume with the alcohol or water.

18. The method of claim 17, wherein the homogeneous solution is filter-sterilized.

19. The method of claim 17, wherein the alcohol is ethanol, the weak organic acid is citric acid, the antioxidant is selected from the group consisting of sodium bisulfite, sodium metabisulfite and combinations thereof, and the chelator is disodium edetate.

* * * * *